United States Patent
Shichiri (10) Patent No.: US 7,829,526 B2
(45) Date of Patent: Nov. 9, 2010

(54) CARDIOINHIBITORY/ANTIHYPERTENSIVE NOVEL ENDOGENOUS PHYSIOLOGICALLY ACTIVE PEPTIDE

(75) Inventor: Masayoshi Shichiri, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 783 days.

(21) Appl. No.: 10/599,479

(22) PCT Filed: Apr. 1, 2005

(86) PCT No.: PCT/JP2005/006510

§ 371 (c)(1),
(2), (4) Date: Dec. 19, 2006

(87) PCT Pub. No.: WO2005/095609

PCT Pub. Date: Oct. 13, 2005

(65) Prior Publication Data

US 2008/0267871 A1    Oct. 30, 2008

(30) Foreign Application Priority Data

Apr. 2, 2004  (JP)  ............... 2004-110463

(51) Int. Cl.
C07K 14/00   (2006.01)
A61K 49/00   (2006.01)
C07H 21/04   (2006.01)

(52) U.S. Cl. ............... 514/2; 514/13; 530/300; 536/23.1

(58) Field of Classification Search ............ 514/2, 514/13; 530/300; 536/23.1
See application file for complete search history.

(56) References Cited

FOREIGN PATENT DOCUMENTS

JP   2004-008027   6/2004
WO   WO 01/32875   * 5/2001
WO   WO 01/32875 A1   5/2001

OTHER PUBLICATIONS

Masayoshi Shichiri et al., Salusins: newly identified bioactive peptides with hemodynamic and mitogenic activities, Nature Medicine, Sep. 2003, pp. 1166-1172, vol. 9, No. 9.
Hua Lou and Robert F. Gagel, Alternative Ribonucleic Acid Processing in Endocrine Systems, Endocrine Reviews, 2001, pp. 205-225, The Endocrine Society, vol. 22, No. 2.
Masayoshi Shichiri, Salusins, Jul. 7, 2004, pp. 267-270, vol. 210, No. 4.
Fang Yu et al., Salusins promote cardiomyocyte growth but does not affect cardiac function in rats, Regulatory Peptides, published online on Aug. 18, 2004, pp. 191-197, No. 122, Elsevier.
Hajime Izumiyama et al., Synthetic Salusins as Cardiac Depressors in Rat, Hypertension, Mar. 2005, pp. 419-425, No. 45, American Heart Association.
International Preliminary Report On Patentability and Written Opinion The International Bureau of WIPO, Oct. 19, 2006, Switzerland corresponding to PCT/JP2005/006510.

* cited by examiner

*Primary Examiner*—Chih-Min Kam
(74) *Attorney, Agent, or Firm*—Locke Lord Bissell & Liddell LLP (57) ABSTRACT

The present invention is to provide a novel peptide having a potent hypotensive activity by inhibiting cardiac contractility, a DNA encoding the peptide, an antibody against the peptide, or a cardioinhibitory/hypotensive agent comprising the peptide as an active ingredient. A search of a genetic data base revealed the presence of a peptide biosynthesized by a processing of unspliced product of TOR2A mRNA. As a result of functional analysis, a peptide hormone exerting a potent bioactivity and expressed abundantly throughout human organs was found. The peptide is hydrophobic with a molecular weight of 2664.02 consisting of 24 amino acids (AIFIFISNTGGKQINQVALEAWRS; SEQ ID NO.: 2) and shows a negative inotropism in rat hearts, as well as a marked systemic hypotensive activity.

5 Claims, 1 Drawing Sheet

SEQUENCE LISTING

```
<160> NUMBER OF SEQ ID NOS: 8

<210> SEQ ID NO 1
<211> LENGTH: 72
<212> TYPE: DNA
<213> ORGANISM: Homo sapiens

<400> SEQUENCE: 1
gccatcttca tcttcatcag caacacgggt ggcaagcaga tcaaccaggt ggcattggag    60
gcgtggcgca gc                                                        72

<210> SEQ ID NO 2
<211> LENGTH: 24
<212> TYPE: PRT
<213> ORGANISM: Homo sapiens

<400> SEQUENCE: 2

Ala Ile Phe Ile Phe Ile Ser Asn Thr Gly Gly Lys Gln Ile Asn Gln
1               5                   10                  15
```

Val Ala Leu Glu Ala Trp Arg Ser
            20

<210> SEQ ID NO 3
<211> LENGTH: 28
<212> TYPE: PRT
<213> ORGANISM: Artificial
<220> FEATURE:
<223> OTHER INFORMATION: salusin-alpha

<400> SEQUENCE: 3

Ser Gly Ala Leu Pro Pro Ala Pro Ala Ala Pro Arg Pro Ala Leu Arg
1               5                   10                  15

Ala Gln Arg Ala Gly Pro Ala Gly Pro Gly Ala Lys
            20                  25

<210> SEQ ID NO 4
<211> LENGTH: 20
<212> TYPE: PRT
<213> ORGANISM: Artificial
<220> FEATURE:
<223> OTHER INFORMATION: salusin-beta

<400> SEQUENCE: 4

Ala Ile Phe Ile Phe Ile Arg Trp Leu Leu Lys Leu Gly His His Gly
1               5                   10                  15

Arg Ala Pro Pro
            20

<210> SEQ ID NO 5
<211> LENGTH: 72
<212> TYPE: DNA
<213> ORGANISM: Rat

<400> SEQUENCE: 5
gccattttca tctttatcag caatactgga ggtgagcaga tcaaccaggt ggccctggag      60
gcatggcgca gc                                                          72

<210> SEQ ID NO 6
<211> LENGTH: 24
<212> TYPE: PRT
<213> ORGANISM: Rat

<400> SEQUENCE: 6

Ala Ile Phe Ile Phe Ile Ser Asn Thr Gly Gly Glu Gln Ile Asn Gln
1               5                   10                  15

Val Ala Leu Glu Ala Trp Arg Ser
            20

<210> SEQ ID NO 7
<211> LENGTH: 1527
<212> TYPE: DNA
<213> ORGANISM: Homo sapiens

<400> SEQUENCE: 7
gcctctgacc gaaatcgggc ctcaaccgga tggcggtggc gaggcacggc taccggccct      60
ggggctcgat cctcgggctg ctcgggctgg ccttggctgc cgccgccgcc tgggacgtgg     120
cttctctgcg ctgcaccttc ggctcgttct gcgaatgcga cttctggccc gacttgccgg     180
gtctggaatg tgacctggct caacacctgg ctggccagca tttggccaag gcccctggtgg    240 tgaagtcact gaaggccttt gtacaggacc agccccccag caagccgttg gtccctttccc    300

```
tgcacggctg acaggcacc gggaagtcct acgttagctc cctgctggca cagcatctct    360
tccgggatgg ccttcgcagc cctcacgtcc atcacttctc ccctatcatc catttcccac    420
atcccagccg cactgagcag tacaagaagg agctcaagag ctgggttcag gggaacctca    480
ctgcctgtgg ccgatccctt ttcctcttcg atgagatgga caagctgcct cctggcctga    540
tggaagtcct gcagcccttc ctgggcccctt cttgggttgt gtatgggacc aactatcgca    600
aagccatctt catctttatc agcaatgctg gtggtgagca gatcaaccag gtggccttgg    660
aggcctggcg cagccacagg gacagggaag aaatcagcct acaggaggtg gagccagtaa    720
tctcccgagc tgtgatggac aaccctcaac atggcttctg gcggtctggc atcatggagg    780
agcacctgct ggacgctgtg gtgcccttcc tcccgctcca gcggcatcac gtgcgccact    840
gcgtactcaa tgagctggct cagttgggcc tggagcccag cgaggaggtg gttcaggcgg    900
tgctggacag caccacctac ttccctgagg tagaacagct cttctcctcc aatggctgca    960
agacagtggc ctcccgactc acattttttcc tctgagaagc ccaggtggca tcgctgcctc   1020
ctctgcctgg tcagagcaaa cacgaaaggc ctgggtggct cctggaagaa atctttccta   1080
agctggttgg caagtgggac ccagagcaca atgttaagat gaagaaaggt gttggccagg   1140
ccaaggaaga aaggtctaga agcatctttg ctaagaaact cctgggtacc ccgcaacctc   1200
acagccgtgc cattgccctg cagtctgagc cttagccttc tcaatgtgaa cggcaactca   1260
gggacgaagg ctcctggctg cttccagctg gggactctta ctggcatgcc ttgtctggct   1320
cctttcccag acctcagccc acagactgtg gctggaccca gcaatccagc taggccaggc   1380
tagcacctca caggttcccc aaatggaagg actcaagcta ctacatgggc ctgaatttca   1440
aagttttttaa ttttgtacaa gagaacagag attaaataaa cttagccttg gtattagaaa   1500
aaaaaaaaaa aaaaaaaaaa aaaaaaa                                        1527
```

```
<210> SEQ ID NO 8
<211> LENGTH: 321
<212> TYPE: PRT
<213> ORGANISM: Homo sapiens

<400> SEQUENCE: 8

Met Ala Ala Ala Thr Arg Gly Cys Arg Pro Trp Gly Ser Leu Leu Gly
1               5                   10                  15

Leu Leu Gly Leu Val Ser Ala Ala Ala Ala Trp Asp Leu Ala Ser
            20                  25                  30

Leu Arg Cys Thr Leu Gly Ala Phe Cys Glu Cys Asp Phe Arg Pro Asp
        35                  40                  45

Leu Pro Gly Leu Glu Cys Asp Leu Ala Gln His Leu Ala Gly Gln His
    50                  55                  60

Leu Ala Lys Ala Leu Val Val Lys Ala Leu Lys Ala Phe Val Arg Asp
65                  70                  75                  80

Pro Ala Pro Thr Lys Pro Leu Val Leu Ser Leu His Gly Trp Thr Gly
                85                  90                  95

Thr Gly Lys Ser Tyr Val Ser Ser Leu Leu Ala His Tyr Leu Phe Gln
            100                 105                 110

Gly Gly Leu Arg Ser Pro Arg Val His His Phe Ser Pro Val Leu His
        115                 120                 125

Phe Pro His Pro Ser His Ile Glu Arg Tyr Lys Lys Asp Leu Lys Ser
    130                 135                 140

Trp Val Gln Gly Asn Leu Thr Ala Cys Gly Arg Ser Leu Phe Leu Phe
```

-continued

```
145                 150                 155                 160
Asp Glu Met Asp Lys Met Pro Pro Gly Leu Met Glu Val Leu Arg Pro
                165                 170                 175
Phe Leu Gly Ser Ser Trp Val Val Tyr Gly Thr Asn Tyr Ala Lys Ala
            180                 185                 190
Ile Phe Ile Phe Ile Ser Asn Thr Gly Gly Lys Gln Ile Asn Gln Val
        195                 200                 205
Ala Leu Glu Ala Trp Arg Ser Arg Arg Asp Arg Glu Ile Leu Leu
    210                 215                 220
Gln Glu Leu Glu Pro Val Ile Ser Arg Ala Val Leu Asp Asn Pro His
225                 230                 235                 240
His Gly Phe Ser Asn Ser Gly Ile Met Glu Glu Arg Leu Leu Asp Ala
            245                 250                 255
Val Val Pro Phe Leu Pro Leu Gln Arg His His Val Arg His Cys Val
            260                 265                 270
Leu Asn Glu Leu Ala Gln Leu Gly Leu Glu Pro Arg Asp Glu Val Val
        275                 280                 285
Gln Ala Val Leu Asp Ser Thr Thr Phe Phe Pro Glu Asp Glu Gln Leu
    290                 295                 300
Phe Ser Ser Asn Gly Cys Lys Thr Val Ala Ser Arg Ile Ala Phe Phe
305                 310                 315                 320
Leu
```

CARDIOINHIBITORY/ANTIHYPERTENSIVE NOVEL ENDOGENOUS PHYSIOLOGICALLY ACTIVE PEPTIDE

This application is a 371 of PCT/JP2005/006510, filed Apr. 1, 2005, which claims the benefit of foreign application JAPAN 2004-110463, filed Apr. 2, 2004.

TECHNICAL FIELD

The present invention relates to a novel cardioinhibitory/hypotensive endogenous bioactive peptide, a DNA encoding the peptide, an antibody against the peptide, and a cardioinhibitory/hypotensive agent comprising the peptide as an active ingredient.

TECHNICAL FIELD

The present inventor previously found salusin-α and salusin-β which are bioactive factors, by a method applying bioinformatics analysis. Salusin-α and salusin-β, related peptides of 28 amino acids (SEQ ID NO: 3), and 20 amino acids (SEQ ID NO: 4), respectively, are biosynthesized by a processing of preprosalusin (PSECO218, HEMBA 1005096, AK075520) which is an alternatively spiced product of Torsin dystoria-family (Torsin family) gene (TOR2A gene) expressed by a frame shift due to deletion of exon 4 (see for example, non-patent document 1). Systemic hemodynamics and aortic vascular effects of a synthesized salusin-α, β on rats were investigated. In other words, synthesized salusin-α and -β were injected intravenously into femoral vein of SD rats (250-300 g) after cannulating femoral artery under pentobarbital anesthesia, to analyze chronological change of blood pressure and heart rates. Moreover, effects of salusin-α and β on vascular tonus were investigated using contracted isolated rat aortic preparation pretreated with phenylephrine.

As a result, both salusin-α and -β induced a rapid hypotensive and bradycardiac effects 1 min after intravenous administration, but the reduced pressure and heart rate returned to a normal level within 10 to 15 min. The hypotensive and bradycardiac effects by salusin-α (1-10 nmol/kg) and salusin-β (0.1-1 nmol/kg) were dose-responsive. The potency of salusin-β was approximately 10-fold greater compared to salusin-α. The hypotensive effects of salusins were not affected by prepreatment with NO synthase inhibitor, L-NAME. Moreover, studies using isolated preparation of rat aorta did not show any direct effect of salusin-α and -β on intact and endothelium-detached preparations unconstricted or constricted with phenylephrine. In addition to the negative vascular effects, since salusins (α and β), endogenous peptides, induce bradycardia together with a potent hypotensive effect, they are considered to be bioactive peptides with a novel hypotensive mechanism.

Further, it is known that adenosine lowers heart rates (negative chronotropic effect) and lowers impulse transmission via A-V nodes (negative transmission effect) (for example, see patent document 1, non-patent document 2) Further, use of particular adenosine A1 agonist belonging to the class of N6-substituted-5'-(N-substituted) carboxyamidoadenosine for treating impairment of heart rhythm in mammals, and a novel dosage form to practice this use have been proposed (for example, see patent document 2).

Patent document 1: U.S. Pat. No. 4,673,563
Patent document 2: Published Japanese translation of PCT international publication No. 2003-514863
Non-patent document 1: Nat Med 9: 1166-72, 2003
Non-patent document 2: Journal of Pharmacology and Experimental Therapeutics 271:1371, 1994

DISCLOSURE OF THE INVENTION

Object to be Solved by the Invention

The object of the present invention is to provide a novel peptide having a potent hypotensive activity by suppressing cardiac contractility, a DNA encoding the peptide, an antibody against the peptide, and a cardioinhibitory/hypotensive agent comprising the peptide as an active ingredient, or the like.

Means to Solve the Object

As mentioned above, the present inventor recently applied bioinformatic analysis of human-secretory protein cDNA library, to identify multifunctional peptides that are estimated to be biosynthesized after alternative splicing and subsequent frame shift, and designated as salusin-α and salusin-β (see non-patent document 1). Although the alternative splicing is evident in many major human organs, the produced mRNA constitutes a portion of the spliced and predominant unspliced product. Therefore, their concentrations in human blood and the specific role of these peptides remain unclear. While searching preprosalusin gene sequence, the present inventor found unspliced TOR2A mRNA and estimated the presence of a putative peptide biosynthesized by a processing, being translated from TOR2A mRNA itself. As a result of functional analyses, the present inventor discovered a peptide hormone with a potent bioactivity that expresses in a larger amount throughout various human organs. This peptide is hydrophobic, with a molecular weight of 2664.02 consisting of 24 amino acids, and shows a negative inotropism in rat hearts, as well as a significant hypotensive activity. The present inventor confirmed that a peptide of high homology, with only one amino acid substituted is expressed in rat and human and shows similar functions.

While the above-mentioned peptide of the present invention is an endogenous hypotensive factor produced in various human organs, similarly to salusin-α and salusin-β, it may be more useful since it is expressed and biosynthized in a larger amount compared to both salusins. Intraveneous administration of this peptide of the present invention into anesthesized rats resulted in a marked lowering of aortic pressure (FIG. 1), reduced heart rates and aortic blood flow. The results revealed this factor to be the most potent endogenous peptide identified thus far showing negative inotropic (FIG. 2) and chronotropic effects. Studies using isolated perfused rat hearts also revealed that the peptide directly acts on heart to potently reduce cardiac contractility. The present invention has been completed based on these findings.

In other words, the present invention relates to (1) a peptide consisting of any one of the following amino acids: (A) the amino acid sequence shown by SEQ ID No: 2; (B) an amino acid sequence wherein one or a few amino acids are deleted, substituted or added in the sequence shown by SEQ ID No: 2, wherein a peptide consisting of the amino acid sequence has a cardioinhibitory activity or hypotensive activity; (C) an amino acid sequence having 60% or more homology with the amino acid sequence shown by SEQ ID No: 2, wherein a peptide consisting of the amino acid sequence has a cardioinhibitory activity or hypotensive activity; (2) a peptide generated from (A) the amino acid sequence shown by SEQ ID No: 2; or (B) an amino acid sequence wherein one or a few amino acids are deleted, substituted or added in the sequence shown by SEQ ID No: 2, as a result of further cleavage or modification by a processing enzyme and having a cardioinhibitory activity or hypotensive activity.

Further, the present invention relates to (3) (A) a DNA encoding a peptide consisting of the amino acid sequence shown by SEQ ID No: 2; (B) a DNA encoding a peptide consisting of an amino acid sequence wherein one or a few amino acids are deleted, substituted, or added in the sequence shown by SEQ ID No: 2, and having a cardioinhibitory activity or hypotensive activity; (C) a DNA encoding a peptide consisting of an amino acid sequence having 60% or more homology with the amino acid sequence shown by SEQ ID No: 2, and having a cardioinhibitory activity or hypotensive activity; (D) a DNA consisting of the nucleotide sequence shown by SEQ ID No: 1; (E) a DNA encoding a peptide consisting of a nucleotide sequence wherein one or a few nucleotides are deleted, substituted or added in the shown by SEQ ID No: 1, and having a cardioinhibitory activity or hypotensive activity; (F) a DNA that hybridizes with the nucleotide sequence shown by SEQ ID No: 1 under a stringent condition, and encoding a peptide having a cardioinhibitory activity or hypotensive activity; (4) a DNA generated from (A) the amino acid sequence shown by SEQ ID No: 2; or (B) an amino acid sequence wherein one or a few amino acids are deleted, substituted or added in the amino acid sequence shown by SEQ ID No: 2, as a result of further cleavage or modification by a processing enzyme and having a cardioinhibitory activity or hypotensive activity.

Further, the present invention relates to (5) a fusion peptide wherein the peptide according to (1) or (2) is bound with a marker protein and/or peptide tag; (6) a recombinant vector comprising the DNA according to (3) wherein the recombinant vector can express the peptide according to (1); (7) a recombinant vector comprising the DNA according to (4), wherein the recombinant vector can express the peptide according to (2); (8) a transformant wherein the recombinant vector according to (6) is introduced, which expresses the peptide according to (1) (9) a transformant wherein the recombinant vector according to (7) is introduced, which expresses the peptide according to (2); (10) an antibody that can recognize specifically the peptide according to (1) or (2); (11) the antibody according to (10) wherein the antibody is a monoclonal antibody; (12) a method for screening a cardioinhibitory factor or hypotensive factor, comprising the steps of administering the peptide according to (1) or (2) and a test substance to a non-human test animal, and measuring/estimating a level of cardioinhibitory activity or hypotensive activity; (13) a method for screening an inhibitor of cardioinhibitory activity or an inhibitor of hypotensive activity, comprising the steps of administering the peptide according to (1) or (2) and a test substance to a non-human test animal, and measuring/estimating a level of cardioinhibitory or hypotensive activity; (14) a cardioinhibitory/hypotensive agent comprising the peptide according to (1) or (2) as an active ingredient; or (15) a method for preventing/treating diseases which requires administration of the cardioinhibitory/hypotensive agent according to (14) via its cardioinhibitory/hypotensive activity.

Effect of the Invention

A peptide of the present invention is a novel endogenous peptide in humans, inhibiting cardiac contractility, and expected to be effective as a hypotensive agent with minimal side-effect. By further investigating the roles of the peptide, future research advance is anticipated for the development of new therapeutic agents, such as β-antagonist mimetics, in the treatment of cardiovascular diseases including angina, and for elucidating the mechanism of cardiac failure/angina.

BEST MODE OF CARRYING OUT THE INVENTION

A peptide of the present invention is not specifically limited as long as it is a peptide consisting of any one of the following amino acids: (A) the amino acid sequence shown by SEQ ID No: 2; (B) an amino acid sequence wherein one or a few amino acids are deleted, substituted or added in the amino acid sequence shown by SEQ ID No: 2, and having a cardioinhibitory activity or hypotensive activity; or (C) an amino acid sequence having 60% or more homology with the amino acid sequence shown by SEQ ID No: 2, and having a cardioinhibitory activity or hypotensive activity; or a peptide generated from (A) the amino acid sequence shown by SEQ ID No: 2; or (B) an amino acid sequence wherein one or a few amino acids are deleted, substituted or added in the amino acid sequence shown by SEQ ID No: 2, as a result of further cleavage or modification by a processing enzyme and having a cardioinhibitory activity or hypotensive activity. Further, a DNA of the present invention is not specifically limited as long as it is any one of the following: (A) a DNA encoding a peptide consisting of the amino acid sequence shown by SEQ ID No: 2; (B) a DNA encoding a peptide consisting of an amino acid sequence wherein one or a few amino acids are deleted, substituted, or added in the sequence shown by SEQ ID No: 2, and having a cardioinhibitory activity or hypotensive activity; (C) a DNA encoding a peptide consisting of an amino acid sequence having 60% or more homology with the amino acid sequence shown by SEQ ID No: 2, and having a cardioinhibitory activity or hypotensive activity; (D) a DNA consisting of the nucleotide sequence shown by SEQ ID No: 1; (E) a DNA encoding a peptide consisting of a nucleotide sequence wherein one or a few nucleotides are deleted, substituted or added in the sequence shown by SEQ ID No: 1, and having a cardioinhibitory activity or hypotensive activity; (F) a DNA that hybridizes with the nucleotide sequence shown by SEQ ID No: 1 under a stringent condition, and encoding a peptide having a cardioinhibitory activity or hypotensive activity; or a DNA encoding a peptide consisting of (A) an amino acid sequence shown by SEQ ID No: 2; or (B) an amino acid sequence wherein one or a few amino acids are deleted, substituted or added in the amino acid sequence shown by SEQ ID No: 2 and having a cardioinhibitory activity or hypotensive activity; generated by a cleavage or modification by a processing enzyme. "A peptide having a cardioinhibitory activity or hypotensive activity" herein mentioned relates to a peptide comprising a negative inotropism/negative chronotropic effect, associated with the inhibition of cardiac contractility, or to a peptide having a hypotensive activity. However, the specific mechanism of action is not specifically limited. Examples of the specific mechanisms include, lowering of aortic pressure, lowering of heart rates/pulse rates, lowering of aortic blood flow rate, lowering of cardiac output, lowering of coronary blood flow and lowering of peripheral blood pressure. However, it is not limited to these examples.

"An amino acid sequence wherein one or a few amino acids are deleted, substituted or added" herein mentioned relates to an amino acid wherein, any number of amino acids, for example, 1 to 10, preferably 1 to 5 amino acids are deleted, substituted or added. Further, "a nucleotide sequence wherein one of a few nucleotides are deleted, substituted or added" mentioned in the above, relates to a nucleotide sequence wherein, any number of nucleotides, for example, 1 to 20, preferably 1 to 15, more preferably 1 to 10, further preferably 1 to 5 nucleotides are deleted, substituted or added. Moreover, as a specific example of an amino acid sequence wherein one or a few amino acids are deleted, substituted or added in the amino acid sequence shown by SEQ ID No: 2, having a cardioinhibitory activity or a hypotensive activity, an amino acid sequence wherein 4 amino acids at C-terminal end are deleted: (1-20); an amino acid sequence wherein 4 amino acids at N terminal end are deleted (5-24), a potent cardioinhibitory activity or hypotensive activity is maintained. In a sequence wherein 11 amino acids at C-terminal end, and 1 amino acid at N-terminal end are deleted (2-13), even the activity is somewhat decreased, it has been confirmed that the cardioinhibitory activity or hypotensive activity is maintained.

For example, a DNA consisting of a nucleotide sequence wherein one or a few nucleotides are deleted, substituted or added (mutant DNA), can be prepared by any conventional methods, such as chemosynthesis, DNA engineering method, or mutagenesis. Specifically, a mutant DNA can be obtained by introducing a mutation to the DNA consisting of the sequence shown by SEQ ID No: 1 by using a method allowing the DNA to contact and react with an agent as a mutagen, a method irradiating ultraviolet ray or a DNA engineering method. Site-specific mutagenesis, which is one of DNA engineering methods, is useful as it is a method that can introduce a specific mutation to a specific site. The method can be performed according to Molecular Cloning: A laboratory Manual, 2nd Ed., Cold Spring Harbor Laboratory, Cold Spring Harbor, N.Y., 1989 (hereinafter referred to as "Molecular Cloning 2nd Ed."), Current Protocols in Molecular Biology, Supplement 1-38, John Wiley & Sons (1987-1997). By expressing the mutant DNA with the use of an appropriate expression system, a peptide consisting of an amino acid sequence wherein one or a few amino acids are deleted, substituted or added can be obtained.

In the present invention, "an amino acid sequence having 60% or more homology with the amino acid sequence shown by SEQ ID No: 2" is not specifically limited as long as the homology with the amino acid sequence shown by SEQ ID No: 2 is 60% or more, for example 60% or more, preferably 70% or more, more preferably 80% or more, further preferably 90% or more, particularly preferably 95% or more, and most preferably 98% or more.

In the present invention, "a nucleotide sequence that hybridizes under a stringent condition" relates to a nucleotide sequence that can be obtained by colony hybridization method, plaque hybridization method, or southern blotting hybridization method, with the use of nucleic acids such as DNA or RNA as a probe. Specifically, a DNA that can be identified by hybridizing at 65° C. in the presence of 0.7 to 1.0 M NaCl, with the use of a filter on which a DNA derived from a colony or a plaque, or a fragment thereof is immobilized, and by washing the filter with a 0.1 to 2-fold SSC solution (one-fold concentration SSC solution is composed of 150 mM sodium chloride and 15 mM sodium citrate) under a condition of 65° C. is exemplified. Hybridization can be performed according to a method described in Molecular Cloning, 2nd Ed. For example, as a DNA that can hybridize under a stringent condition, a DNA having a certain homology with the nucleotide sequence of the DNA used as a probe. A DNA having for example 60% or more, preferably 70% or more, more preferably 80% or more, further preferably 90% or more, particularly preferably 95% or more, and most preferably 98% or more homology can be preferably exemplified.

A method for obtaining or preparing a DNA of the present invention is not specifically limited. A desired DNA can be prepared by isolating the DNA by screening a cDNA library that is expected to contain the DNA with the use of an appropriate probe or primer prepared according to the amino acid sequence or nucleotide sequence information shown by SEQ ID No: 1 or 2 disclosed in the present invention, or by chemosynthesis according to a common procedure.

Specifically, a DNA expressing the peptide of the present invention can be obtained by first preparing a human cDNA library according to a common procedure since cDNA of the present invention derived from human tissue, preparing an appropriate probe specific to the DNA of the present invention from the library according to the sequence information of TOR2A genes, and selecting the desired clone by using the probe. Origins of the above cDNA include various cells or tissues derived from animals including human and rats. Further, isolation of total RNA from these cells or tissues, as well as isolation or purification of mRNA, acquisition of cDNA and cloning thereof, can all be performed according to a common procedure. For example, methods for screening a DNA of the present invention from a cDNA library includes those described in Molecular Cloning, 2nd Ed. The nucleotide sequence of a DNA of the present invention derived from human is exemplified as SEQ ID No: 1, and the nucleotide sequence of a DNA of the present invention derived from rat is exemplified as SEQ ID No: 5. Moreover, the nucleotide sequence of TOR2A gene is exemplified as SEQ ID No: 7.

A mutant DNA or homologous DNA of the present invention comprising the nucleotide sequence shown by any one of the above (B) to (F), can be isolated by using a nucleotide sequence shown by SEQ ID No: 1 or a DNA fragment comprising a part thereof, and screening under a certain condition a homolog of the DNA from other organisms and the like. Further, it can be prepared by a method of preparing a mutant DNA, described in the above.

A method for obtaining/preparing a peptide of the present invention is not specifically limited, and it can be a naturally occurring peptide, chemosynthesized peptide, or a recombinant peptide prepared by DNA recombination technology. When obtaining a naturally occurring peptide, a peptide of the present invention can be obtained by combining appropriate methods for isolating/purifying a peptide from cells or tissues expressing the peptide. When preparing a peptide by chemosynthesis, a peptide of the present invention can be synthesized according to chemosynthesis method such as Fmoc method (fluorenylmethyloxycarbonyl method), tBoc method (t-butyloxycarbonyl method). Moreover, a peptide of the present invention can be synthesized by using various commercial peptide synthesizers. When preparing a peptide by DNA recombination technology, a peptide of the present invention can be prepared by introducing a DNA consisting of the nucleotide sequence encoding the peptide into a suitable expression system.

When preparing a peptide of the present invention by DNA recombination technology, in order to collect and purify the peptides from cell cultures, conventional methods including ammonium sulfate or ethanol precipitation, acid extraction, anion or cation chromatography, phosphocellulose chromatography, hydrophobic interaction chromatography, affinity chromatography, hydroxy apatite chromatography and lectin chromatography can be used, and high performance liquid chromatography is preferably used. Especially, as a column used in affinity chromatography, by using a column bound with an antibody such as monoclonal antibodies against a peptide of the present invention, or when a normal peptide tag is added to the above-mentioned peptide of the present invention, a column bound with a substance having affinity to the peptide tag, purified materials of these peptides can be obtained.

Furthermore, the peptides of the present invention comprising the human-derived amino acid sequence shown by SEQ ID No: 2, peptides consisting of an amino acid sequence wherein one or a few amino aids are deleted, substituted, or peptides consisting of an amino acid sequence having 60% or more homology with the amino acid sequence shown by SEQ ID No: 2, can be appropriately prepared or obtained by a person skilled in the technique using the information of the nucleotide sequence SEQ ID No: 1 encoding the amino acid sequence, SEQ ID No: 2. For example, it can be isolated by screening under an appropriate condition a homolog of the DNA from an organism other than human, with the use of the sequence SEQ ID No: 1 or a DNA comprising a part thereof, as a probe. Moreover, a peptide encoded by the homolog DNA can be produced by cloning a full-length DNA of the homolog DNA, and subsequently integrating it into an expression vector to express it in an appropriate host. The amino acid sequence of a peptide of the present invention derived from rats is exemplified as SEQ ID No: 6. Further, for reference, the amino acid sequence of TOR2A is exemplified as SEQ ID No: 8.

The above peptide generated from (A) the amino acid sequence shown by SEQ ID No: 2; or (B) an amino acid sequence wherein one or a few amino acids are deleted, substituted or added in the amino acid sequence shown by SEQ ID No: 2, as a result of further cleavage or modification by a processing enzyme and having a cardioinhibitory activity or hypotensive activity, can be obtained easily by synthesizing various peptides including the N-terminal region of the peptide consisting of the amino acid sequence shown by SEQ ID No: 2, and by screening their cardioinhibitory activity or hypotensive activity; or by detecting human serum by using an antibody that recognizes specifically the N-terminal region of the peptide consisting of the amino acid sequence shown by SEQ ID No: 2. Further, a DNA consisting of the sequence encoding the peptide can be easily prepared according to the amino acid sequence information of the peptide.

A fusion peptide of the present invention is not specifically limited as long as a peptide of the present invention is bound with any maker protein and/or peptide tag. A marker protein is not specifically limited if it is conventionally known, including enzymes such as alkaline phosphatase and HRP, Fc region of the antibody, and fluorescent substances such as GFP. Specific examples of peptide tags of the present invention include epitope tags such as HA, FLAG and Myc; affinity tags such as GST, maltose-binding protein, biotinylated peptide and oligohistidine, which are conventionally known peptide tags. The fusion peptides can be prepared by a common procedure, and are useful for purifying a peptide of the present invention using the affinity of Ni-NTA and His tag, detecting a peptide of the present invention, quantifying an antibody against a peptide of the present invention, and also as a research reagent for the present invention.

A recombinant vector of the present invention is not specifically limited as long as it comprises a DNA of the present invention mentioned above and can express a peptide of the present invention mentioned above. A recombinant vector of the present invention can be constructed by integrating appropriately a DNA of the present invention into, for example, an expression vector for animal cell expression. An expression vector should preferably be self-replicable in host cells, or could be recombined into chromosomes of host cells. Further, an expression vector comprising a regulatory sequence such as a promoter, enhancer or terminator, at a suitable position where a DNA of the present invention can be expressed, can be preferably used. Additionally, an expression system could be any system as long as it can express a peptide of the present invention in host cells, and include the following: expression systems derived from chromosome, episome and virus, for example, vectors derived from bacterial plasmid, yeast plasmid, papovavirus such as SV40, vaccinia virus, adenovirus, fowl poxvirus, pseudorabies virus or retrovirus; vectors derived from bacteriophage, transposon, or from a combination thereof, for example those derived from genetic elements of plasmid and bacteriophage such as cosmids and phagemids.

A transformant of the present invention is not specifically limited as long as it is introduced a recombinant vector of the present invention mentioned above and can express a peptide of the present invention mentioned above. Examples include transgenic yeast, transgenic plants (cells, tissues, individuals), transgenic bacteria, transgenic animals (cells, tissues, individuals), while transgenic animal cells are preferable. Examples of animal host cells include Namalva cells, COS1 cells, COS7 cells and CHO cells. As a method for introducing a recombinant vector into animal cells, for example, electroporation method, calcium phosphate method and lipofection method can be used.

As to an antibody specifically recognizing a peptide of the present invention, an antibody binding specifically to a peptide of the present invention is preferable. Examples of such antibodies include immune-specific antibodies such as monoclonal antibodies, polyclonal antibodies, chimeric antibodies, single-stranded antibodies and humanized antibodies. These can be prepared by a common procedure by using a peptide of the present invention as an antigen, while among these, monoclonal antibodies are preferable for its specificity, and polyclonal antibodies are preferable for its sensitivity. Antibodies binding specifically to a peptide of the present invention such as monoclonal antibodies and polyclonal antibodies are useful for elucidating a pathophysiological value of a peptide of the present invention in various diseases, diagnosing diseases caused by a mutation or deletion of a peptide of the present invention, or revealing a molecular mechanism of a peptide of the present invention.

An antibody against a peptide of the present invention is produced by administering a fragment comprising the peptide or epitope to an animal (preferably other than human) by using conventional protocols. For example, when preparing a monoclonal antibody, any method including hybridoma method (Nature 256, 495-497, 1975); trioma method, human B cell hybridoma method (Immunology Today 4, 72, 1983), and EBV-hybridoma method (MONOCLONAL ANTIBODIES AND CANCER THERAPY, pp. 77-96, Alan R. Liss, Inc., 1985) can be used. In the following, a method for preparing a monoclonal antibody binding specifically to a peptide of the present invention derived from a mouse, by taking a peptide derived from human as an example of a peptide of the present invention, will be explained.

A monoclonal antibody of the present invention can be produced by culturing the monoclonal antibody-producing hybridoma by a common procedure, in vivo or in vitro. For example, in an in vivo system, it can be obtained by culturing in a peritoneal cavity of rodents, preferably mouse or rat, and in an in vitro system, it can be obtained by culturing in a medium for culturing animal cells. As a medium for culturing hybridomas in an in vitro system, a cell culture medium such as RPMI1640 or MEM comprising antibiotics such as streptomycin or penicillin can be exemplified.

As a monoclonal antibody-generating hybridoma of the present invention mentioned in the above, a hybridoma generating a monoclonal antibody of the present invention can be produced by immunizing a BALB/c mouse with a peptide of the present invention obtained from human or rat, by performing cell fusion of spleen cells of the immunized mouse and mouse NS-1 cells (ATCC TIB-18) according to a common procedure and screening by immunofluorescent staining patterns. Further, a method for separating/purifying the monoclonal antibody can be any method that is used generally for purifying peptides or proteins, and liquid chromatography such as affinity chromatography can be specifically exemplified.

In order to produce a single-strand antibody against a peptide of the present invention mentioned in the above of the present invention, a method for preparing a single-strand antibody (U.S. Pat. No. 4,946,778) can be applied. Further, in order to express a humanized antibody, it is possible to use a transgenic mouse or other mammals, to separate/isolate clones expressing a peptide of the present invention, or to purify a peptide of the present invention by affinity chromatography, by using the above antibody. An antibody against a peptide of the present invention is useful to elucidate the molecular mechanism of a peptide of the present invention.

Further, functional analysis of a peptide of the present invention can be advantageously performed by using fluorescent substances such as FITC (Fluoresceinisothiocyanate) or tetramethylrhodamine isocyanate, radioisotopes such as $^{125}I$, $^{32}P$, $^{14}C$, $^{35}S$, or $^{3}H$, or those labeled with enzymes such as alkaline phosphatase, peroxidase, β-galactosidase or phycoerythrin, or fusion proteins fused with fluorescent luminescent proteins such as Green fluorescent protein (GFP). Furthermore, as a method of immunological measurement by using an antibody of the present invention, RIA method, ELISA method, fluorescent antibody method, plaque method, spot method, hemagglutination reaction method, or Ouchterlony method can be exemplified.

As a screening method of the present invention, it is not specifically limited as long as it is designed to obtain cardioinhibitory or hypotensive factors or inhibitors of cardioinhibitory or hypotensive activity, comprising the steps of administering a peptide of the present invention derived from human or rats to a non-human test animal model such as rat or mouse with a test substance, and measuring/estimating a level of cardioinhibitory activity or hypotensive activity. Specifically, cardioinhibitory factors or hypotensive factors, or inhibitors of cardioinhibitory or hypotensive activity can be screened by administering a test substance orally or parenterally, before or after, or at the same time of administering a peptide of the present invention intransvenously to a non-human test animal such as rats or mice, measuring a level of cardioinhibitory activity such as lowering of blood pressure, aortic pressure, pulse rates, or aortic blood flow rate, and comparing/estimating with a measurement level of a control without being administered a test substance. Examples of the above test substances include natural products such as substances extracted from animals/plants or microorganisms, compounds obtained by chemosynthesis, various bioactive peptides or proteins, or various hypotensive agents or hypertensive agents which are conventionally known as well as various adjuvants. A substance promoting cardioinhibitory activity obtained by a screening method of the present invention is highly possible to be useful as a hypotensive agent when it is used alone or simultaneously with a peptide of the present invention. Further, an inhibitor of cardioinhibitory activity is highly possible to be useful as a cardiotonic or hypertensive agent when it is used alone or simultaneously with a peptide of the present invention. Moreover, these substances promoting or inhibiting cardioinhibitory activity are useful for studying the action mechanism of cardioinhibitory/hypotensive activity in vivo.

A cardioinhibitory/hypotensive agent of the present invention is not specifically limited as long as it comprises a peptide of the present invention as an active ingredient. Further, a method for preventing/treating diseases that necessitate cardioinhibitory or hypotensive activity of the present invention is not specifically limited as long as it is a method comprising the step of administering a cardioinhibitory/hypotensive agent of the present invention to a patient necessitating cardioinhibitory activity or hypotensive activity. "A cardioinhibitory activity or hypotensive activity" herein mentioned relates to an activity inhibiting cardiac function, including lowering of blood pressure, lowering of aortic pressure, lowering of pulse rates and lowering of aortic blood flow rate. A cardioinhibitory/hypotensive agent of the present invention can be used advantageously for preventing or treating diseases including hypertension, angina, cardiac failure, arrhythmia and hypertrophic cardiomyopathy, as it has a cardioinhibitory activity.

When using such cardioinhibitory/hypotensive agent as a drug, various prescribed compounds such as pharmaceutically acceptable normal carrier, bonding agent, stabilizing agent, excipient, diluent, pH buffer agent, disintegrator, solubilizer, dissolving adjuvant, and isotonic agents can be added. The agent can be administered orally or parenterally. In other words, it can be administered orally in a dosage form which is generally used, for example in form of powder, granule, capsule, syrup, suspension, or parenterally for example in form of solution, emulsion, suspension by an injection. Moreover, it can also be administered in nostril in form of spray. Parenteral administration is preferable. In administering parenterally, aqueous solvents such as distilled water and saline, dissolving adjuvants such as sodium salicylate, isotonic agents such as sodium chloride, glycerin, D-mannitol, stabilizing agents such as human serum albumin, preservatives such as methyl paraben, local anesthetics such as benzyl alcohol, can be compounded.

The dosage of a cardioinhibitory/hypotensive agent of the present invention can be selected appropriately depending on types of diseases, body weight or age of the patient, reagent form, symptoms, etc. For example, when administering to an adult, it is preferable to administer a peptide of the present invention or a pharmaceutically acceptable salt thereof which is an active ingredient, in an amount of about 0.01 to 100 nmol/kg, preferably 0.05 to 30 nmol/kg, more preferably 0.1 to 10 nmol/kg per dosage, and it is preferable to administer this amount 1 to 3 times a day. When administering parenterally a cardioinhibitory/hypotensive agent of the present invention, it can be administered for example, intravenously, subcutaneously, intramuscularly, in a cavitas medullaris, or mucosally, while intravenous or subcutaneous administration is preferable.

In the following, the present invention will be explained more specifically by referring to the Examples, while the technical scope of the present invention is not limited to these exemplifications.

EXAMPLE 1

Preparation of a Peptide of the Present Invention

The peptide of the present invention consisting of the amino acid sequence (AIFIFISNTGGKQINQVALEAWRS) shown by SEQ ID No:2 was found as follows. When salusin was discovered, it was already expected that a preprosalusin, a precursor of salusin, was generated as a result of an alternative splicing and deletion of exon 4' of a TOR2A gene which consists of 5 exons as evident from a GenBank registered clone (AL162426 Human DNA sequence from clone RP11-56D16 on chromosome 9, complete sequence, April 2001; Length=163338). The TOR2A gene is widely expressed throughout various human organs. A small portion of the transcript becomes spliced into preprosalusin while great majority is expressed as TOR2A mRNA except that in vascular endothelial cells and vascular smooth muscle cells preprosalusin is abundantly expressed. Investigation of an amino acid sequence translated from TOR2A mRNA revealed a sequence predicted to be biosynthesized by prohormone convertase, or carboxypeptitase E. Thus, a full-length TOR2A cDNA sequence was cloned by PCR, subcloned into pTarget vector (Promega), introduced into cultured vascular endothelial cells to perform a gene expression experiment. A hypotensive activity secreted in the culture supernatant was confirmed in an in vivo experimental system using rats as mentioned above. Fractionation of the hypotensive activity by gel filtration chromatography corresponded to the results of molecular weight fractionation of the peptide shown by SEQ ID No: 2.

Meanwhile, a peptide of the present invention consisting of the amino acid sequence shown by SEQ ID No: 2 determined in Example 1, was synthesized with the use of a peptide synthesizer (Shimadzu, PSSM-8), and tested in the following experiment. SD rats weighing 400 to 525 g were used as test animals.

EXAMPLE 2

Effect of a Synthesized Peptide of the Present Invention on Intact-Rats

Figure 1:
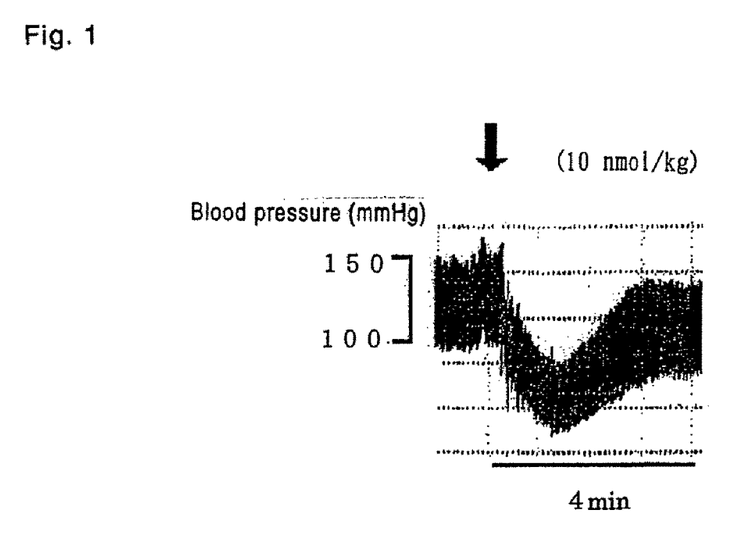

SD rats were anesthetized by intraperitoneal pentobarbital sodium (50 mg/kg), and a synthesized peptide was administered intravenously via a catheter placed in the femoral artery. Heart rates and blood pressure were measured according to a method described previously (Nat Med 9: 1166-72, 2003) with the use of an electromagnetic flowmeter (MFV-1100, Nihon Koden). Further, a flowmeter was attached to the abdominal aorta, and aortic flow was measured according to the above method described previously. Synthetic peptides (10 nmol/kg) were administered intravenously over a period of 15 seconds or more, and systolic pressure (SP), diastolic pressure (DP) mean aortic pressure (MAP), heart rate (HR) were measured. Results of hypotensive effects are shown in FIG. 1. A hypotensive effect of a synthetic peptide of the present invention was observed.

EXAMPLE 3

Effect of a Synthetic Peptide of the Present Invention on Isolated Hearts

Figure 2:
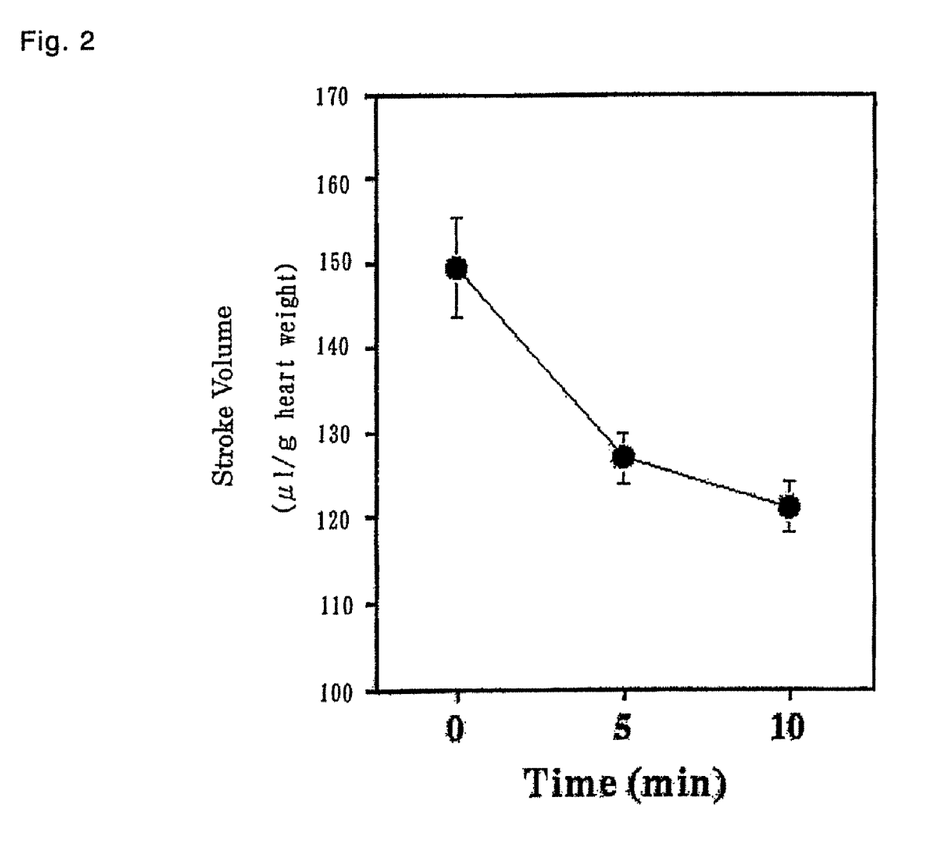

Isolated heart working model was used for estimating direct effect on cardiac muscle, according to a method described previously (Nat Med 9:1169-72, 2003). A heart isolated from a rat was set on an isolated heart perfusion apparatus (Primetech Corporation, IPH-W2) which was perfused with a Krebs Henseleit Buffer at 37° C., and stabilized. Subsequently, synthetic peptides were administered ($10^{-8}$ mol/l). Then, HR, SP, DP, MAP and aortic flow (AF) were measured over a period of 15 min. Coronary flow (CF) was measured by collecting coronary sinus effluent before and at 5 and 10 min after administering the peptide agent. Based on the obtained data, cardiac output (CO) was calculated by adding AF and CF, whereas stroke volume (SV) was obtained by dividing CO by HR, and then normalized by the heart volume of each rat. Results of coronary flow are shown in FIG. 2. As a result, an effect of lowering coronary flow of a synthetic peptide of the present invention was observed.

BRIEF DESCRIPTION OF DRAWINGS

[FIG. 1]

It is a figure showing a hypotensive effect of a synthetic peptide of the present invention in intact-rats.

[FIG. 2]

It is a figure showing a time course of change of stroke volume of isolated, perfused rat hearts by a synthetic peptide of the present invention.

---

The invention claimed is:

1. An isolated peptide consisting of any one of the following amino acid sequence (A) to (D):
   (A) the amino acid sequence shown by SEQ ID NO: 2;
   (B) the amino acid sequence shown by position 1 to 20 of SEQ ID NO: 2;
   (C) the amino acid sequence shown by position 5 to 24 of SEQ ID NO: 2; and
   (D) the amino acid sequence shown by position 2 to 13 of SEQ ID NO: 2.

2. A fusion peptide comprising the peptide according to claim 1 and a marker protein, a peptide tag or a combination thereof.

3. A method for screening a cardioinhibitory factor or hypotensive factor, comprising the steps of administering an effective amount of the peptide according to claim 1 and a test substance to a non-human test animal, measuring a level of cardioinhibitory activity or hypotensive activity, and estimating the test substance as a cardioinhibitory factor in case that cardioinhibitory activity is higher when administering said peptide and said test substance than when administering the same amount of said peptide only, or estimating the test substance as a hypotensive factor in case that hypotensive activity is higher when administering said peptide and said test substance than when administering the same amount of said peptide only.

4. A method for screening an inhibitor of cardioinhibitory activity or an inhibitor of hypotensive activity, comprising the steps of administering an effective amount of the peptide according to claim 1 and a test substance to a non-human test animal, measuring a level of cardioinhibitory or hypotensive activity, and estimating the test substance as an inhibitor of cardioinhibitory activity in case that cardioinhibitory activity is lower when administering said peptide and said test substance than when administering the same amount of said peptide only, or estimating the test substance as an inhibitor of hypotensive activity in case that hypotensive activity is lower when administering the same amount of said peptide and said test substance than when administering said peptide only.

5. A cardioinhibitory/hypotensive agent comprising the peptide according to claim 1 as an active ingredient.

* * * * *